United States Patent [19]
Lush et al.

[11] Patent Number: 4,877,920
[45] Date of Patent: Oct. 31, 1989

[54] PROCESS FOR REMOVING ARSINE IMPURITIES IN PROCESS STREAMS

[75] Inventors: Richard A. Lush, Wilmington, Del.; Hsiang-Wei Tsao, West Chester, Pa.

[73] Assignee: Sun Refining and Marketing Company, Philadelphia, Pa.

[21] Appl. No.: 203,847

[22] Filed: Jun. 8, 1988

[51] Int. Cl.$^4$ ................................................ C07C 7/12
[52] U.S. Cl. ...................................... 585/823; 208/253
[58] Field of Search ......................... 585/823; 208/253

[56] References Cited

U.S. PATENT DOCUMENTS 3,542,669  11/1970  DeFeo .................................. 585/823
4,462,896  7/1984  Kitagawa et al. ................... 585/823

*Primary Examiner*—Curtis R. Davis
*Attorney, Agent, or Firm*—J. Edward Hess; Donald R. Johnson

[57] ABSTRACT

A process for removing arsenic contaminants from a hydrocarbon fluid by contacting the fluid with copper oxide supported on activated carbon.

9 Claims, No Drawings

PROCESS FOR REMOVING ARSINE IMPURITIES IN PROCESS STREAMS

SUMMARY

The invention is an improved method of removing arsenic from hydrocarbon streams and comprises treating the hydrocarbon with copper oxide (CuO) deposited on activated carbon.

BACKGROUND OF THE INVENTION

The presence of arsenic in its various chemical forms as an impurity in feed stocks and finished products can be detrimental to their use. For example, arsenic in very small quantities in a hydrocarbon stream can poison the noble metal catalysts frequently used to further process the stream by oxidation, polymerization, catalytic cracking and the like.

Since most crude oils contain arsenic in one form or another, the hydrocarbon fractions derived from cracking, fractionating or otherwise separating these raw materials will also contain arsenic. Volume concentrations of as little as one part of arsenic per million (ppm) may render some hydrocarbon streams unacceptable for further processing. For example, with present high yield catalysts for propylene polymerization, even 50 parts of arsenic per billion (ppb) in a propylene feed will poison the catalyst in a short time. For this reason, various methods of arsenic removal have been developed but improved processes are still desired.

DESCRIPTION OF THE PRIOR ART

It is known to remove arsenic from hydrocarbons by contact with CuO, either alone or supported on alumina. See for example U.S. Pat. Nos. 4,593,148, 3,789,581 and 4,462,896. It is also known to use activated carbon for this purpose, as described in U.S. Pat. No. 3,542,669. However, the combination of CuO on activated carbon, which gives unexpectedly superior results, has not, to our knowledge, been disclosed.

DETAILED DESCRIPTION OF THE INVENTION

The hydrocarbon stream treated in accordance with the invention is normally obtained from petroleum but can also be obtained from other sources such as natural gas. Normally it will contain 1–10 carbon atoms preferably 2–6, more preferably it is a $c_2-c_6$ olefin such as ethylene or propylene. The amount of arsenic in the stream is not critical but best results are obtained when it is 50–300 ppb (by weight). Although it is believed that a major portion of the arsenic contained in hydrocarbon fluids and inert gases is present as arsine ($AsH_3$), or lower hydrocarbyl arsines ($R_xAsH_{3-x}$, where R is an alkyl radical containing 1–4 carbon atoms and x is 0, 1, 2 or 3), as well as the metal (As), the term "arsenic" as used herein is intended to include arsenic in any combined form which is a gas or liquid at ambient conditions.

The treating agent or sorbent used in our invention is easily prepared. The activated carbon is obtained from any of the numerous commercial suppliers. The copper oxide is deposited thereon by known means such as treating with an aqueous salt or the hydroxide and then calcining in air. Most activated carbon suppliers will make up the CuO containing activated carbon, if requested. The amount of CuO mainly affects catalyst life and is not critical. It will usually be 5–25%. The surface area of the activated carbon is preferably greater than 350 $m^2$/gm, more preferably 500 $m^2$/gm.

The treatment of the hydrocarbon is done in liquid or vapor phase but is preferably liquid phase. The space velocity is not critical but is usually 1–1000 volumes of hydrocarbon (liquid equivalent) per volume of activated carbon per hour preferably 1–100. The main effect of space velocity is on efficiency of arsenic removal, as is well known.

The treatment is easily effected by passing the arsenic-containing hydrocarbon stream through a bed of the activated carbon, preferably under pressure to maintain liquid phase operation, and preferably at ambient temperature, although higher temperatures such as 100°–200° C. can be used. Numerous processing schemes and types of apparatus are shown in the prior art and will be readily apparent to those skilled in the art. See, for example, U.S. Pat. Nos. 4,593,148 and 3,833,498.

The exact mechanism of arsenic removal is not known, that is, it is not known whether it reacts with the copper oxide, whether the copper oxide catalyzes a reaction between arsine and traces of sulfur in the hydrocarbon fluid, whether adsorption is involved with or without any of these other mechanisms, or the like.

EXAMPLES

The arsine-containing stream was prepared by bubbling a mixture of $AsH_3$ in nitrogen, available as a bottled gas, into a container of liquified polymer grade propylene which was kept at ambient temperature and pressurized with nitrogen to keep the hydrocarbon below its boiling point. The sorbent being tested was placed in a 1 inch diameter, 12 inch long stainless steel cylinder fitted with ¼" outlets. The arsine containing propylene was fed by pressure differential through a separate 1" pretreatment bed of the same size containing ZnO/CaO pellets to remove as much $H_2S$ as possible before passing through the test sorbent. The propylene as fed to the test sorbent contained 10–12 ppb each of hydrogen sulfide, mercaptan sulfur and carbonyl sulfide. The space velocity was 40 volumes of liquid per volume of sorbent per hour.

The results of experiments using the copper oxide on carbon of this invention are shown in Table I along with comparable runs using a pure carbon support without copper oxide and a copper oxide supported on alumina. Copper oxide alone was not used in the comparative experiments because it would be a powder which would either plug up the apparatus entirely or would be washed out of the apparatus along with the propylene. The copper oxide on alumina was therefore utilized as a surrogate for copper oxide alone since the alumina structure has a low surface area which will allow the activity of copper oxide to dominate and thus approach the value expected for a pure copper oxide sorbent alone. Alumina by itself has essentially no arsine removal capability. The copper oxide on alumina also allows direct comparison of this sorbent as disclosed by Carr, et al in U.S. Pat. No. 3,789,581.

The CuO on alumina was obtained from United Catalysts, Inc. (UCI), Louisville, KY. It is in the form of pellets 3/16"×3/16" and contains 10–12% CuO on gamma alumina. The surface area is 187 $m^2$/gm. and the pore volume is 0.4 cc/gm.

The CuO on activated carbon, also obtained from UCI, contains 13% CuO, 86% C, and 1% unidentified metals. It has a pore volume of 2-3 cc/gm., a surface area of 550-800 in 2/gm., and a pore volume of 2-3 cc/gm.

The following results were achieved:

TABLE I

| Run | Sorbent | Arsine Feed | Content-ppb Product* |
|---|---|---|---|
| 1 | CuO on alumina | 64 | 23-29 |
| 2 | Act. carbon | 100 | 72—72 |
| 3 | CuO on act. carbon | 61 | 1-7 |
| 4 | CuO on act. carbon | 100 | 6-9 |
| 5 | CuO on alumina | 1366 | 117-166 |
| 6 | Act. carbon | 1500 | 57-139 |
| 7 | CuO on act. carbon | 1340 | 36-69 |

*range for 12 runs

As shown in Table I, both copper oxide on alumina (Runs 1 and 5) and activated carbon alone (Runs 2 and 6) reduce arsine content, but the copper oxide on carbon of the present invention shows a surprising improvement over either of these similar materials. The advantage of the copper oxide on carbon is most pronounced at lower arsine contamination levels (Runs 1-4) which would be typical of, for example, lighter hydrocarbon process streams. However, even at the high arsine levels (Runs 5-7) typical of heavier refinery streams, the present invention shows an improvement over the copper oxide on alumina or carbon alone.

In another run, propylene as described above has been passed over a catalyst like the above for eleven months. The arsine content of the propylene has averaged 180 ppb and the average liquid hourly space velocity has been 15.5. To date, the arsine in the product has tested zero and 125,000 turnovers of catalyst have occurred. A turnover is the passage through a reactor filled with the treating agent of one reactor volume of liquid propylene.

It will be apparent from the above examples that the arsenic contents as low as 20 ppb, more preferably under 5 ppb, can be achieved with the novel treating agent disclosed herein. In terms of turnovers, 50,000 are readily achieved, more often more than 100,000, with arsenic contents as mentioned.

We claim:

1. A process for reducing the arsenic content of a hydrocarbon-containing fluid which comprises contacting said fluid with copper oxide supported on activated carbon.

2. Process according to claim 1 wherein the hydrocarbon comprises a $C_2$-$c_6$ alkane or alkene.

3. Process according to claim 1 or 2 wherein said arsenic content is reduced to less than 5 ppb by weight.

4. Process according to claim 1 or 2 wherein the said supporting material has a surface area in excess of 500 $m^2/g$.

5. Process according to claim 1 or 2 wherein said contacting is in the liquid phase.

6. Process according to claim 1 or 2 wherein said arsenic comprises arsine.

7. Process according to claim 1 or 2 wherein the arsenic content of the treated hydrocarbon fluid is less than 20 ppb after 50,000 turnovers of the copper oxide.

8. Process according to claim 7 wherein aid arsenic content is 5 ppb and said number of turnovers is 100,000.

9. Process according to claim 1 wherein said hydrocarbon containing fluid also contains sulfur.

* * * * *